(12) United States Patent
Laufer (10) Patent No.: US 6,273,907 B1
(45) Date of Patent: *Aug. 14, 2001

(54) BRONCHIAL STENTER

(75) Inventor: Michael D. Laufer, Menlo Park, CA (US)

(73) Assignee: Broncus Technologies, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/833,550

(22) Filed: Apr. 7, 1997

(51) Int. Cl.$^7$ ........................................ A61F 7/00

(52) U.S. Cl. ................ 607/96; 607/98; 607/101

(58) Field of Search .................. 607/98, 96, 101, 607/113, 124; 606/15, 28, 31

(56) References Cited

U.S. PATENT DOCUMENTS

| | | |
|---|---|---|
| 3,995,617 | 12/1976 | Watkins et al. . |
| 4,116,589 | 9/1978 | Rishton . |
| 4,129,129 | 12/1978 | Armine . |
| 4,502,490 | 3/1985 | Evans et al. . |
| 4,522,212 | 6/1985 | Gelinas et al. . |
| 4,557,272 | * 12/1985 | Carr . |
| 4,567,882 | 2/1986 | Heller . |
| 4,584,998 | 4/1986 | McGrail . |
| 4,621,882 | 11/1986 | Krumme . |
| 4,625,712 | 12/1986 | Wampler . |
| 4,646,737 | 3/1987 | Hussein et al. . |
| 4,674,497 | 6/1987 | Ogasawara . |
| 4,683,890 | 8/1987 | Hewson . |
| 4,704,121 | 11/1987 | Moise . |
| 4,709,698 | 12/1987 | Johnston et al. . |
| 4,772,112 | 9/1988 | Zider et al. . |
| 4,779,614 | 10/1988 | Moise . |
| 4,802,492 | 2/1989 | Grunstein . |
| 4,817,586 | 4/1989 | Wampler . |
| 4,825,871 | 5/1989 | Cansell . |
| 4,846,152 | 7/1989 | Wampler et al. . |
| 4,895,557 | 1/1990 | Moise et al. . |
| 4,906,229 | 3/1990 | Wampler . |
| 4,920,978 | 5/1990 | Colvin . |
| 4,944,722 | 7/1990 | Carriker et al. . |
| 4,955,377 | 9/1990 | Lennox et al. . |
| 4,969,865 | 11/1990 | Hwang et al. . |
| 4,976,709 | 12/1990 | Sand . |
| 4,985,014 | 1/1991 | Orejola . |
| 4,991,603 | 2/1991 | Cohen et al. . |
| 5,009,936 | 4/1991 | Yamanaka et al. . |

(List continued on next page.)

FOREIGN PATENT DOCUMENTS

| | | |
|---|---|---|
| 0 282 225 | 9/1988 | (EP) . |
| 0 286 145 | 10/1988 | (EP) . |
| 0 768 091 | 4/1997 | (EP) . |
| 2 233 293 | 1/1991 | (GB) . |
| 0 545 358 | 7/1977 | (SU) . |
| WO 98/44854 | 10/1998 | (WO) . |
| WO 99/03413 | 1/1999 | (WO) . |

Primary Examiner—John P. Leubecker
Assistant Examiner—Roy Gibson
(74) Attorney, Agent, or Firm—Morrison & Foerster LLP (57) ABSTRACT

A device and method for treating collapsed bronchial tubes found in patients with chronic obstructive pulmonary disease and asthma are provided. The device includes an elongated member having a heating element that includes one or more energy delivery members. The method includes heating the bronchial tube to cause at least a portion of the cross links of the collagen in the wall to unlink/open and subsequently form new cross links after the collagen fibers have realigned. The procedure effectively reinforces the structural integrity of the wall and thereby prevents the lumen from collapsing.

9 Claims, 5 Drawing Sheets

U.S. PATENT DOCUMENTS

| | | |
|---|---|---|
| 5,019,075 | 5/1991 | Spears et al. . |
| 5,036,848 | 8/1991 | Hewson . |
| 5,053,033 | 10/1991 | Clarke . |
| 5,084,044 * | 1/1992 | Quint ..................................... 606/27 |
| 5,096,916 | 3/1992 | Skupin . |
| 5,103,804 | 4/1992 | Abele et al. . |
| 5,105,826 | 4/1992 | Smits et al. . |
| 5,167,223 | 12/1992 | Koros et al. . |
| 5,191,883 | 3/1993 | Lennox et al. . |
| 5,213,576 | 5/1993 | Abiuso et al. . |
| 5,231,996 | 8/1993 | Bardy et al. . |
| 5,232,444 | 8/1993 | Just et al. . |
| 5,234,456 | 8/1993 | Silvestrini . |
| 5,255,678 | 10/1993 | Deslauriers et al. . |
| 5,255,679 | 10/1993 | Imran . |
| 5,269,758 | 12/1993 | Taheri . |
| 5,293,869 | 3/1994 | Edwards et al. . |
| 5,309,910 | 5/1994 | Edwards et al. . |
| 5,313,943 | 5/1994 | Houser et al. . |
| 5,345,936 | 9/1994 | Pomeranz et al. . |
| 5,368,591 | 11/1994 | Lennox et al. . |
| 5,374,287 | 12/1994 | Rubin . |
| 5,393,207 | 2/1995 | Maher et al. . |
| 5,400,778 | 3/1995 | Jonson et al. . |
| 5,415,166 | 5/1995 | Imran . |
| 5,423,811 | 6/1995 | Imran et al. . |
| 5,433,730 | 7/1995 | Alt . |
| 5,443,470 | 8/1995 | Stern . |
| 5,456,667 | 10/1995 | Ham et al. . |
| 5,458,596 | 10/1995 | Lax et al. . |
| 5,465,717 | 11/1995 | Imran et al. . |
| 5,471,982 | 12/1995 | Edwards et al. . |
| 5,478,309 | 12/1995 | Sweezer et al. . |
| 5,496,311 | 3/1996 | Abele et al. . |
| 5,509,419 | 4/1996 | Edwards et al. . |
| 5,545,161 | 8/1996 | Imran . |
| 5,545,193 | 8/1996 | Fleischman et al. . |
| 5,549,559 | 8/1996 | Eshel . |
| 5,562,608 | 10/1996 | Sekins et al. . |
| 5,571,074 | 11/1996 | Buckman, Jr. et al. . |
| 5,578,072 | 11/1996 | Barone et al. . |
| 5,588,432 | 12/1996 | Crowley . |
| 5,588,812 | 12/1996 | Taylor et al. . |
| 5,595,183 | 1/1997 | Swanson et al. . |
| 5,601,088 | 2/1997 | Swanson et al. . |
| 5,605,157 | 2/1997 | Panescu et al. . |
| 5,607,462 | 3/1997 | Imran . |
| 5,630,425 | 5/1997 | Panescu et al. . |
| 5,641,326 | 6/1997 | Adams . |
| 5,680,860 | 10/1997 | Imran . |
| 5,681,308 | 10/1997 | Edwards et al. . |
| 5,707,218 | 1/1998 | Maher et al. . |
| 5,707,336 | 1/1998 | Rubin . |
| 5,707,352 | 1/1998 | Sekins et al. . |
| 5,722,401 | 3/1998 | Pietroski et al. . |
| 5,722,403 | 3/1998 | McGee et al. . |
| 5,722,416 | 3/1998 | Swanson et al. . |
| 5,727,569 | 3/1998 | Benetti et al. . |
| 5,730,741 | 3/1998 | Horzewski et al. . |
| 5,740,808 | 4/1998 | Panescu et al. . |
| 5,752,518 | 5/1998 | McGee et al. . |
| 5,755,714 | 5/1998 | Murphy-Chuthorian . |
| 5,755,753 | 5/1998 | Knowlton . |
| 5,759,158 | 6/1998 | Swanson . |
| 5,765,568 | 6/1998 | Sweezer et al. . |
| 5,769,846 | 6/1998 | Edwards et al. . |
| 5,779,698 * | 7/1998 | Clayman et al. ..................... 606/39 |
| 5,782,797 | 7/1998 | Schweich, Jr. et al. . |
| 5,782,848 | 7/1998 | Lennox . |
| 5,782,899 | 7/1998 | Imran . |
| 5,792,064 | 8/1998 | Panescu et al. . |
| 5,795,303 | 8/1998 | Swanson et al. . |
| 5,800,375 | 9/1998 | Sweezer et al. . |
| 5,807,306 | 9/1998 | Shapland et al. . |
| 5,810,757 | 9/1998 | Sweezer et al. . |
| 5,820,554 | 10/1998 | Davis et al. . |
| 5,827,277 | 10/1998 | Edwards . |
| 5,833,651 | 11/1998 | Donovan et al. . |
| 5,843,075 * | 12/1998 | Taylor ..................................... 606/34 |
| 5,848,969 | 12/1998 | Panescu et al. . |
| 5,855,577 | 1/1999 | Murphy-Chuthorian et al. . |
| 5,860,974 * | 1/1999 | Abele ..................................... 606/41 |
| 5,865,791 | 2/1999 | Whayne et al. . |
| 5,871,443 | 2/1999 | Edwards et al. . |
| 5,873,865 | 2/1999 | Horzewski et al. . |
| 5,881,727 | 3/1999 | Edwards . |
| 5,882,346 | 3/1999 | Pomeranz et al. . |
| 5,904,651 | 5/1999 | Swanson . |
| 5,904,711 | 5/1999 | Flom et al. . |
| 5,908,445 | 6/1999 | Whayne et al. . |
| 5,908,446 | 6/1999 | Imran . |
| 5,919,172 | 7/1999 | Golba, Jr. . |
| 5,954,661 | 9/1999 | Greenspon et al. . |
| 5,954,662 | 9/1999 | Swanson et al. . |
| 5,964,753 | 10/1999 | Edwards . |
| 5,964,796 | 10/1999 | Imran . |
| 5,971,983 | 10/1999 | Lesh . |
| 5,984,971 | 11/1999 | Fleischman et al. . |
| 5,991,650 | 11/1999 | Swanson et al. . |
| 5,992,419 | 11/1999 | Sterzer et al. . |
| 5,993,462 | 11/1999 | Pomeranz et al. . |
| 6,004,269 * | 12/1999 | Crowley et al. ..................... 600/439 |
| 6,024,740 | 2/2000 | Lesh et al. . |
| 6,036,687 | 3/2000 | Laufer et al. . |

\* cited by examiner

BRONCHIAL STENTER

FIELD OF THE INVENTION

The present invention relates to a device and method for treatment of the airway obstruction found in chronic obstructive pulmonary diseases (COPD), such as cystic fibrosis, chronic bronchitis, emphysema, and asthma.

BACKGROUND OF THE INVENTION

Chronic obstructive pulmonary diseases (COPD), which includes such entities as cystic fibrosis, chronic bronchitis, and emphysema, are steadily increasing in frequency, possibly due to continued smoking, increasing air pollution, and the continued aging of the population. COPD is characterized by edema of the mucous membranes, which line the interior walls of the tracheobronchial tree. When the mucosa accumulates an abnormal quantity of liquid, the profuse and thickened serous fluid excreted may seriously affect ventilation in the alveoli. The mucus resists movement up the walls of the tracheobronchial tree, normally efficiently accomplished by the cilia throughout the airways which are also destroyed. Consequently, the serous fluid can form mucus plugs, which can shut off alveoli or entire airways. In addition to secretion accumulation, airway obstruction can occur because the tubes collapse due to destruction of connective tissue. This reduces the ability to get oxygen into the blood and carbon dioxide out of the blood.

Asthma is the most common form of bronchoconstrictive disease and pathologically involves constriction of the bronchioles, hypertrophy of the muscles of the bronchioles, and a characteristic infiltrate of eosinophils. Both asthma and COPD are characterized by the constriction or collapse of airway passages in the lungs that are not supported by cartilage. This condition is marked by labored breathing accompanied by wheezing, by a sense of constriction in the chest, and often by attacks of coughing and gasping. Individuals who are afflicted may attempt to compensate by blowing harder only to have the airways collapse further. A person with poor resulting ventilation suffers from a number of metabolic conditions including accumulation of carbon dioxide. These individuals also often have hyperinflated enlarged lungs and barrel-shaped chests.

A wide variety of drugs are available for treating the symptoms of COPD but none is curative. Cystic fibrosis, chronic bronchitis, and emphysema are typically treated with agents to thin and dry up the secretions and with antibiotics to combat infection and with bronchodilators. These drugs include potassium iodide, antihistamines, various antibiotics, beta agonists and aminophylline. Unfortunately, a large number of patients are not responsive to these medications or become non-responsive after prolonged periods of treatment. For severe cases involving collapsed air passages, surgeons have endeavored to alleviate this disabling condition by either (1) removing a portion of the lungs or (1) constricting the volume of lung available for respiration by stapling off sections thereof. The result is that functionally the diaphragm and muscles in the chest wall operate on a smaller lung volume which may improve air movement for some individuals. These operations are quite risky and are associated with a large number of deaths. Patients undergoing these treatments are quite ill and these procedures are considered final options.

Notwithstanding the conventional treatments available, there exists a need in the art for an effective treatment for chronic obstructive pulmonary diseases, such as cystic fibrosis, chronic bronchitis, emphysema and asthma. Specifically, there is a need for effective treatment for individuals with obstructed airway passages to restore pulmonary function which only requires minimal surgery.

SUMMARY OF THE INVENTION

The present invention is based in part on the discovery that the structural integrity of bronchial tubes, especially those which do not have significant amounts of cartilage present, can be significantly recreated by subjecting the bronchial tubes to a sufficient amount of heat in a specific pattern to cause at least a portion of the cross links of the collagen fibers to open and subsequently form new cross links after the collagen fibers have realigned thereby causing the tubes to remain patent. This procedure changes the structure of the integral collagen and the shape of the tube.

In one aspect, the invention is directed to a method of selectively treating parts of a bronchial tube having a collapsed or partially collapsed lumen which includes the step of heating the inner wall of the lumen to a temperature effective to cause collagen in the wall to undergo a structural transformation.

In a preferred embodiment, the bronchial tube is heated to a temperature in the range between about 40° C. and about 95° C. for about 1 to about 120 seconds. In another preferred embodiment, heating the bronchial tube causes the inner surface of the bronchial tube to form a series of patency bands thereby preventing the bronchial tube from collapsing.

In another aspect, the invention is directed to an apparatus for treating an affected bronchial tube having a collapsed or partially collapsed lumen which includes a heating device comprising an elongated member and having one or more energy delivery members, e.g. electrodes, preferably on the exterior surface of the elongated member, wherein each energy delivery member has sufficient width so that when energized causes collagen in the bronchial tube wall to undergo a structural transformation to restore sufficient rigidity and strength to the wall to enable the bronchial tube to support a substantially non-obstructed lumen; and a source of energy and conduit for conducting energy to the treating element.

In a preferred embodiment, the apparatus includes a plurality of electrodes each spaced apart from an adjacent electrode.

BRIEF DESCRIPTION OF THE DRAWINGS

As used herein, like reference numerals will designate similar elements in the various embodiments of the present invention wherein.

DETAILED DESCRIPTION OF THE PREFERRED EMBODIMENTS

This invention is useful for treating subjects experiencing difficulty in breathing as a result of obstructed airway passages caused, for example, by chronic obstructive pulmonary disease, including, for example, cystic fibrosis, chronic bronchitis, emphysema, and asthma. This invention ameliorates the effects of these diseases by improving lung function by keeping the airway passages open. Specifically, the present invention provides a device and method for effecting changes in collagen-containing soft tissue in the bronchial tubes or air passages of the lungs which have collapsed. The causes of the collapse may be the destruction of the connective tissue, the disease process, swelling, and/or muscle-dependant constriction. The invention is directed to a treatment process which effectively creates an internal bronchial stent which prevents the air passages from collapsing. As used herein, the term "bronchial tube" or "air passage" refers to the sub-segments that branch from the main stem bronchus of the lungs. Cartilage is not present around these air passages in appreciable amounts to prevent the air passage from collapsing.

Figure 1A:
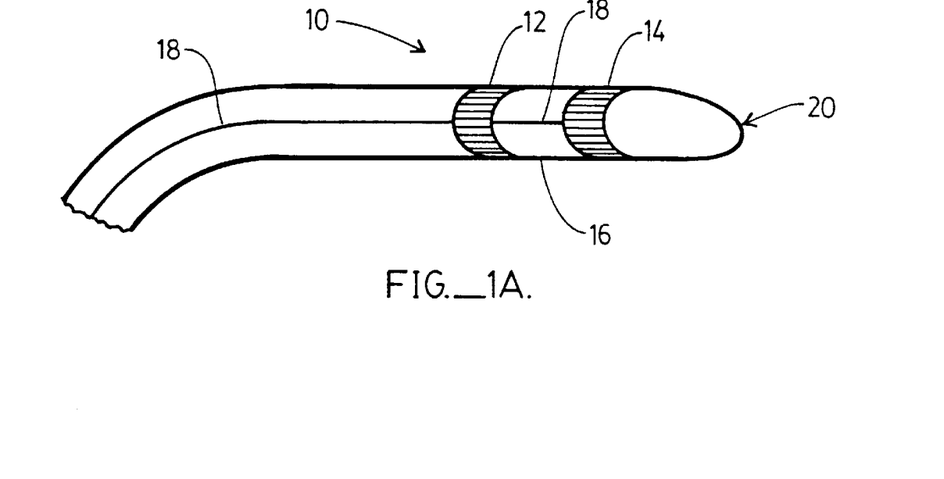
FIGS. 1A, 1B, 2A, 2B, 3A and 3B are perspective views of the heating elements of the inventive treatment apparatus.

FIG. 1 illustrates a preferred embodiment of the inventive treatment apparatus which includes an elongated, cylindrical member 10 having a heating element that has a plurality of electrodes designated 12 and 14 located on the outer surface of the member. The electrodes are electrically connected to a source of RF energy via connector 18. Preferably each electrode is configured as a band as shown that has a width of about 0.2 mm to about 3 mm and preferably each electrode band is separate from the next by a distance of about 0.5 mm to 10 mm. It is understood that the heating element comprises one or more electrode bands. The apparatus has a distal end 20 that is parabolically-shaped to reduce the amount of resistance encountered when the apparatus is advanced into the air passages.

The apparatus has an outer diameter that is approximately equal to (or can be expandable to equal) the desired final inner diameter of the lumen of an obstructed air passage to be treated. Typically, the outer diameter ranges from about 3 French to about 20 French. When the heating element comprises a plurality of electrode bands, the distance between each band is preferably less than about three times the outer diameter of the apparatus. The effect will be that the patency bands formed on the wall of the lumen will be separated from each other by no more than a distance equal to about three times the length of the outer diameter of the lumen. The patency bands so configured will provide good support for the bronchial tube to prevent the lumen from collapsing.

The function of the treating element is to apply a sufficient amount of energy to the walls of collapsible air passages to cause collagen in the walls to undergo a structural transformation to create more rigid walls that can support a non-collapsed, patent lumen. In this embodiment, energy emanates from the electrode bands, so that following treatment with this particular apparatus, the walls of the air passage will develop patency bands corresponding to locations along the walls where the collagen structural transformation has occurred. The contours of the patency bands should substantially match those of the electrode bands. As is apparent, the number and width of each electrode band are not critical. In the case where there is only one electrode band, it may be necessary to move the apparatus and heat more than one area of the lumen wall in order to transform sufficient amounts of the collagen to render the air passage patent. The term "patent" refers to heat treated air passages wherein the lumen remains substantially open during normal breathing.

The heating element is made of any suitable biocompatible material such as, for example, conductive polymer, stainless steel, platinum, other noble metals, or shape memory alloy, such as nickel-titanium-alloy (Nitinol™ commercially available from Raychem Corporation, Menlo Park, Calif.). Member 10 is made of a flexible material so that it can be maneuvered through a catheter or bronchoscope as described herein. The term "catheter" refers generally to a tubular device suitable for insertion into the bronchial tubes. A bronchoscope is a modified catheter which is an illuminating instrument for inspecting and passing instruments (e.g., treatment device) into the bronchial tubes.

When the treatment apparatus is positioned at the treatment site, an RF generator is activated to provide suitable RF energy, preferably at a selected frequency in the range of 10 MHz to 1000 MHz. The emitted energy is converted within the tissue into heat in the range of about 40° C. to about 95° C. As the temperature increases, it is believed that the collagen undergoes a structural transformation whereby the collagen fibers contract and new cross links are formed. Heating creates bands to keep the lumen open. The result of heating with an electrode band or row of electrodes configured substantially around the perimeter of the elongated member is that the connective tissue containing the collagen is transformed into a ring-like, patency band circumscribing the surface of the lumen. The patency band has a diameter that is approximately equal to the outer surface diameter of the corresponding electrode bands or rows of electrodes, however, because of the expected shrinkage associated with the heating process, the patency band may have a circumference that is less than that of the non-treated inner surface. The patency band which is more rigid than the collapsed wall of the air passage prior to treatment effectively prevents the lumen from collapsing once the heating apparatus is removed.

RF energy is no longer applied after there has been sufficient transformation, e.g., shrinkage, of the collagen fibers which may be gauged by removing the heating device from the treatment site and visually determining whether the lumen remains uncollapsed. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method.

Substantial transformation may be achieved very rapidly, depending upon the specific treatment conditions. Because the transformation can proceed at a rather rapid rate, the RF energy should be applied at low power levels. Preferably, the RF energy is applied for a length of time in the range of about 1 seconds to about 120 seconds. Suitable RF power sources are commercially available and well known to those skilled in the art. In one embodiment the RF generator employed has a single channel, delivering approximately 1 to 10 watts of RF energy and possessing continuous flow capability. The rate of transformation can be controlled by varying the energy delivered to the heating element.

Figure 1B:
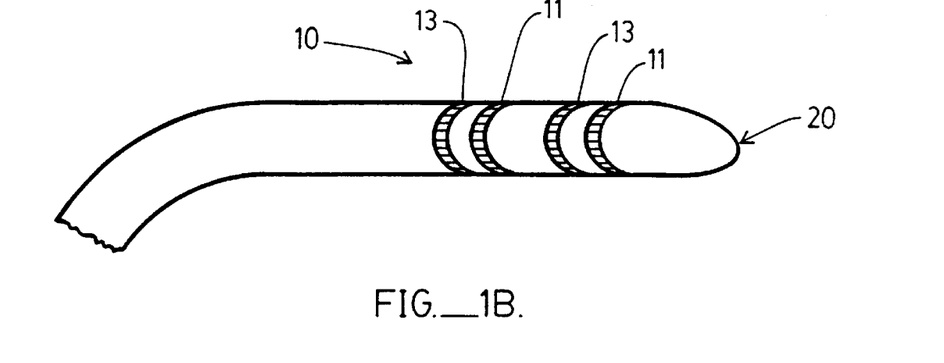
Figure 1C:
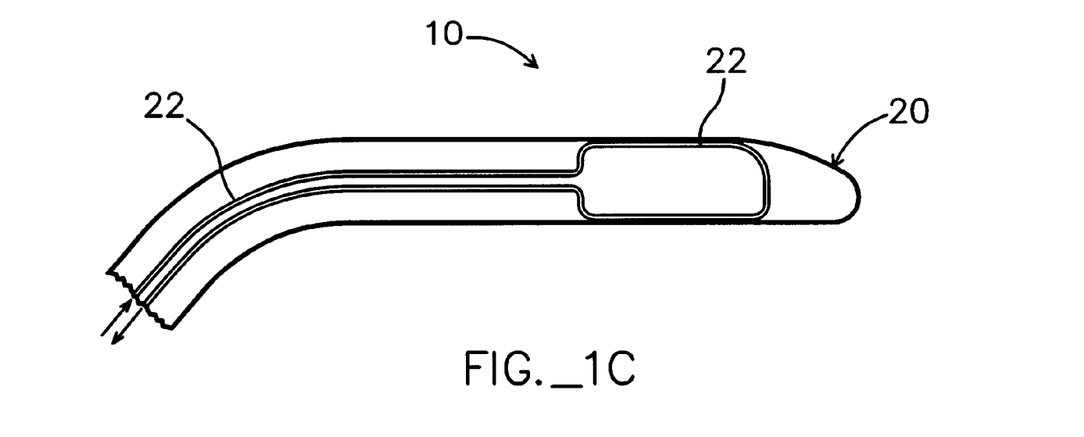
FIG. 1C is a cross-sectional view of an alternative embodiment of the treatment apparatus.

Besides using RF energy for energizing the heating element, it is to be understood that other forms of energy such as alternating current, microwaves, ultrasound, and light either coherent (e.g., laser) or incoherent (e.g., light emitting diode or tungsten filament) can be used, and that the thermal energy generated from a resistive coil, a hot fluid element (e.g., circulating liquids, gases, combinations of liquids and gases, etc.), a curie point element, or similar elements can be used as well. The hot fluid element may comprise, for example, an elongated member 10 as shown in FIG. 1C that includes a conduit system 22 whereby heated fluid is transported through the center of the member and then channeled outward toward the inner surface of the member. In one embodiment the heated fluid is diverted to contact the inner surface of the elongated member so that energy radiates from selected areas on the outer surface of the member corresponding to areas 12 and 14 in FIG. 1A. Regardless of the source, energy delivered to the lumen wall of the obstructed airway passage should be such that none of the tissue is ablated.

The heating element, as shown in FIG. 1, operates as a unipolar, internal electrode in the patient's body. An outer electrode (not shown) having a much larger surface area than that of the electrode bands is placed on the outer surface of the patient's body. For example, an external metal mesh or solid plate is placed on the skin. Both electrodes are connected to an RF generator which produces an electric field at a high frequency within the patient's body. Because the collective surface area of the electrode bands is much smaller than that of the outer electrode, the density of the high frequency electric field is much higher around the electrode bands. The electric field reaches its highest density between the two electrodes in the region near the heating element. The increased density of the field around the electrode bands produces localized heating of the tissue of the lumen wall.

A heating element comprising a bipolar electrode can also be used. Referring to FIG. 1A, in a bipolar arrangement electrode band 12 would be a first conductive element and electrode band 14 would be a second conductive element. The electrode bands emit RF energy with the first conductive element acting as the active electrode and the second conductive element acting as the return electrode, or vice versa. One electrode would be connected to the positive electrode of the generator and the other would be connected to the negative electrode. An insulator 16 is located between the conductive elements. FIG. 1B illustrates a heating element having multiple, i.e., double, bipolar electrode bands. Bands 11 are connected to the positive electrode of the RF generator and bands 13 are connected to the negative electrode. The material between the conductive elements are electrically insulated.

While the heating elements have been shown as electrode bands, other configurations can be used such as, for example, spiral, ring and grid patterns. These elements will create corresponding patterns on the lumen wall. One limitation is that the heating elements have sufficient surface area in contact with the wall of the lumen so that the heat treatment process can be completed within a reasonable time. As is apparent, the heating elements which are in contact with the lumen wall also keep the air passage open during treatment. Since the formation of patency bands that circumscribe the walls of the lumen is expected to provide good mechanical support which prevents a treated air passage from collapsing, preferably the heating elements are configured so that patency bands can be created.

Figure 2A:
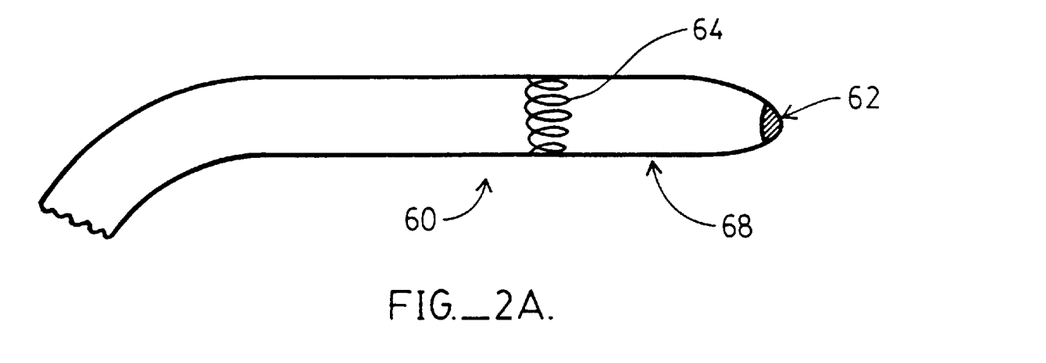

FIG. 2A illustrates another embodiment of the treatment apparatus comprising an elongated, cylindrical member 60 having a heating element that comprises electrodes 62 and 64 located on the other surface of the member. Preferably, the heating element comprises a bipolar electrode wherein one of the electrodes is the active electrode and the other electrode is the return electrode, or vice-versa. One electrode is connected to the RF positive electrode of the generator and the other is connected to the negative electrode. Segment 68 of the member situated between the electrodes is made of electrically insulating material.

Figure 2B:
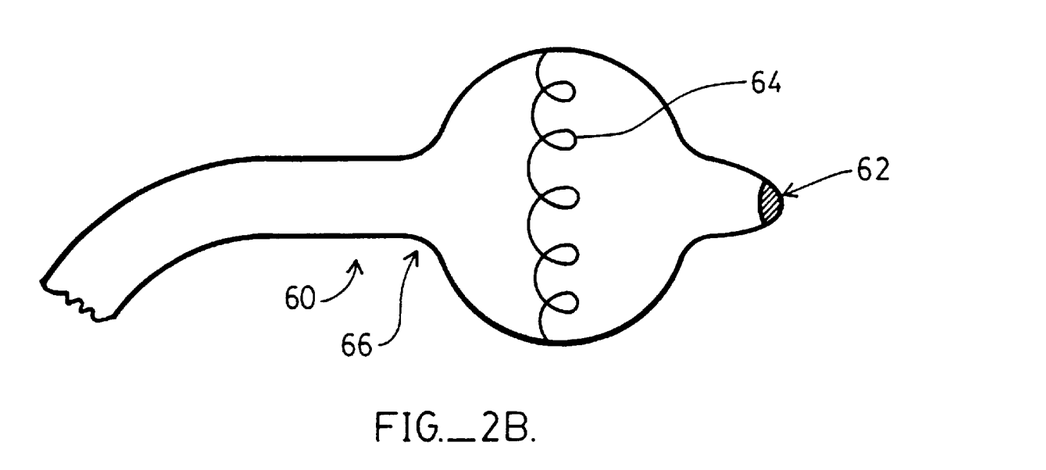

The segment of elongated member in and around electrode 64 is fabricated of material that is expandable and substantially impervious to air or other suitable gases for causing the elongated member to balloon. In this fashion, this section of the elongated member is radially expandable and deformable in response to compressed gas or any other suitable force or material that is applied into the interior region of the elongated member. Moreover, the elongated member will substantially return to its original, non-expanded form when the internal force is deactivated or the material is withdrawn. FIG. 2B illustrates the elongated member in the expanded position. The degree of expansion or distance that the member expands will depend on, among other things, the pressure applied and the elasticity of the member wall. In this embodiment, material between position 66 on the elongated member to the base of electrode 62 is fabricated from expandable material such as latex or polyethylene. The material selected must not melt at the temperature ranges used in the treatment.

Radial expansion causes electrode 64 to come into thermal or electrical contact with an air passage to be treated. Electrode 64 is preferably a spring coil. The treatment apparatus may comprise more than one such coil electrode which are positioned along the length of the elongated member so that a plurality of locations along a bronchial tube can be treated simultaneously.

Figure 3A:
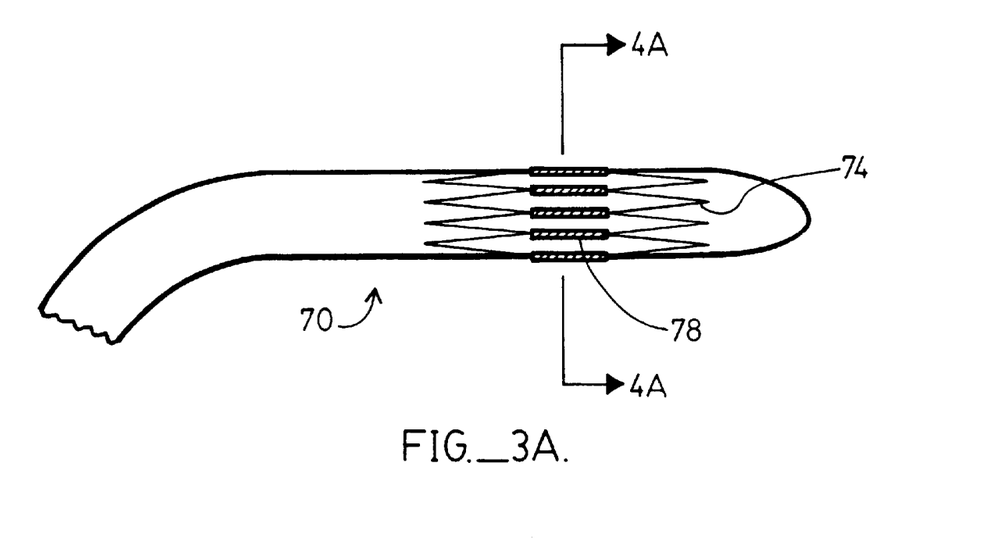
Figure 3B:
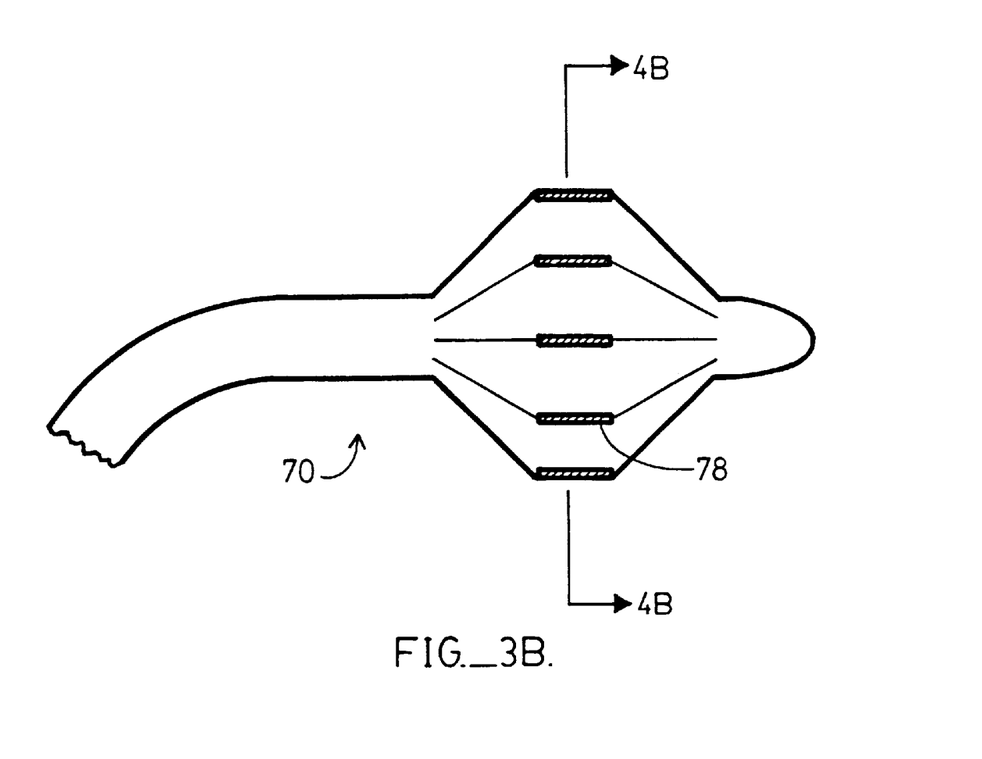
Figure 4A:
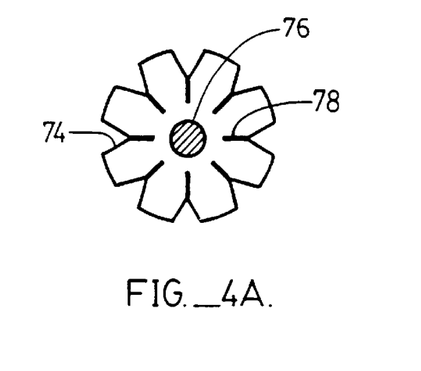
FIGS. 4A and 4B are cross-sectional views of a heating element.
Figure 4B:
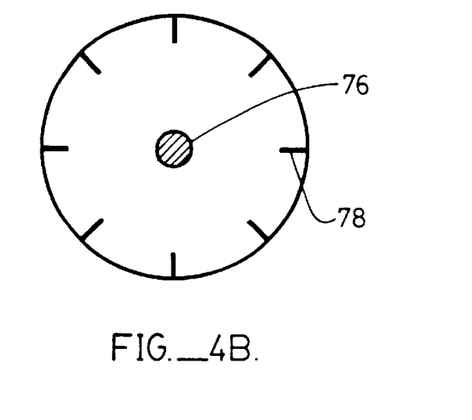

FIG. 3A illustrates a further embodiment of the treatment apparatus comprising an elongated, cylindrical member 70 having one or more electrodes 78 situated on the outer surface of the elongated member. Preferably, a plurality of these electrodes form a number of rows of electrodes that are positioned along the length of the elongated member. As shown in cross sectional view FIG. 4A, the segment of surface of the elongated member at and around the electrodes is arranged in pleats 74. By being folded in this manner, the surface can expand radially when an outward force is applied from the interior of the cylindrical member as shown in FIGS. 3B and 4B. In this embodiment, the electrodes comprise non-ferrous (e.g., aluminum) strips and an electromagnet 76 which is positioned in the interior of the elongated member. When the electromagnetic is energized with alternating current the magnetic field will cause the non-ferrous electrodes to repel from the electromagnet. In addition, the temperature of the electrode will rise due to Joule heating. The treatment apparatus may comprise a plurality of rows of the electrodes.

Figure 5:
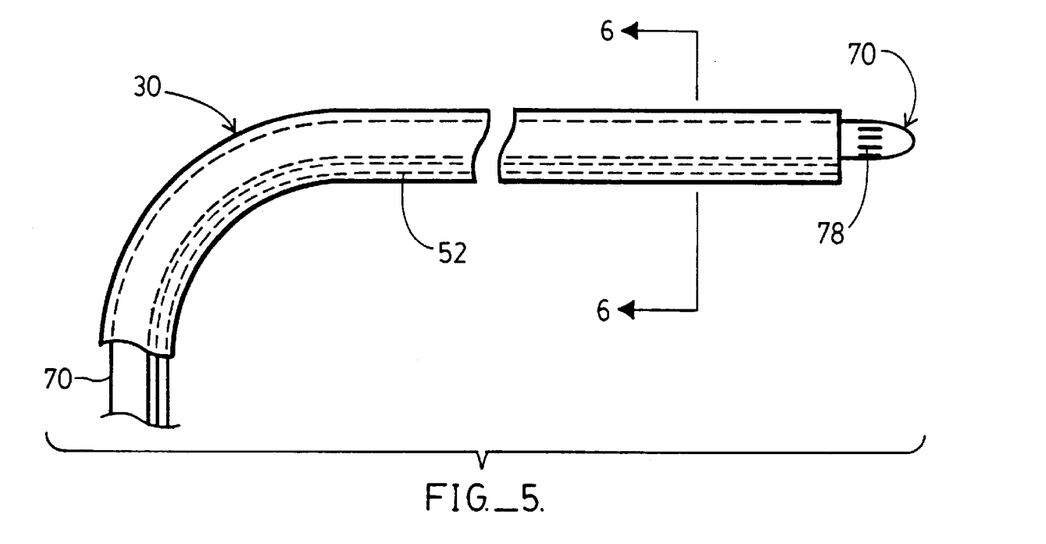
FIGS. 5 and 6 are cross-sectional views illustrating a bronchoscope with a treatment apparatus device positioned therein.
Figure 6:
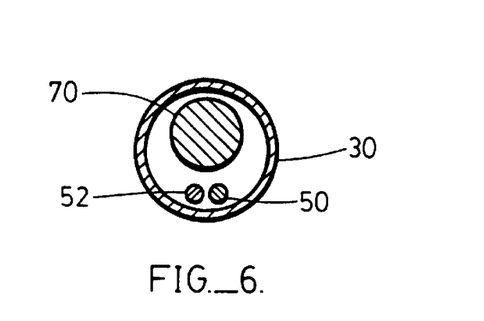

FIGS. 5 and 6 illustrate a bronchoscope 30 having treatment apparatus 70 slidably positioned within a lumen. The device also includes an image-transmitting fiber 50 and illuminating fiber 52. Any conventional bronchoscope with an appropriately sized and directed working lumen may be employed. The image transmitting fiber collects light from the distal end of the treating apparatus and directs the light to a viewing apparatus (not shown) for displaying an image of the obstructed air passage. The bronchoscope may have a panning system which enables the tips to be moved in different directions.

In operation, when treating a person with obstructed air passages, a preliminary diagnosis is made to identify the obstructed air passages that can be treated. In treating a particular site, excessive fluid is first removed from the obstructed air passage by conventional means such as with a suction catheter. Thereafter, the bronchoscope as illustrated in FIG's 5 and 6 is advanced from the person's nasal or oral cavity, and through the trachea, main stem bronchus, and into an obstructed air passage. The heat treatment device is connected to an RF generator located remotely from the patient.

The treatment device is advanced forward from the bronchoscope to expose electrodes 78 before the electromagnetic is energized. Depending on the number of bands or rows of the electrodes, the treatment device can be moved to another position for further heat treatment of the air passage. This process can be repeated as many times as necessary to form a series of patency bands supporting an air passage. This procedure is applied to a sufficient number of obstructed air passages until the physician determines that he is finished. As is apparent, the procedure can be completed in one treatment or multiple treatments. After completion of each treatment, current to the electromagnet is discontinued thereby causing the expanded surface at and near the electrodes to retract radially. The bronchoscope is then removed from the patient.

The heating apparatus can be made to provide protection against verheating of the connective tissue which will cause the collagen to denature. Temperature monitoring and impedance monitoring can be utilized in a system which provides feedback to the user in the form of sounds, lights, other displays or which shuts down the application of energy from the heating element to the treatment site when sufficient transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as modulate the power. The microprocessor can serve as a controller to monitor the temperature and modulate the power.

The invention is also directed to the demonstration or instruction of the inventive surgical techniques including, but not limited to, actual instructions involving patients, audio-visual presentations, animal demonstrations, and the like.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. An apparatus for treating a bronchial tube having a collapsed or partially collapsed lumen which comprises:

a treatment device comprising an elongated member having a heating element at a distal end that comprises one or more electrodes, comprising non-ferrous material, which when energized causes the wall of the lumen to undergo a structural transformation effective to render the wall capable of supporting a non-collapsed lumen, wherein a distal segment of the elongated member comprises expandable material, wherein the one or more electrodes are positioned on an outer surface of the segment, and wherein the treatment device further comprises an electromagnet located in an interior region of said segment; and a source of energy that is conducted to the electromagnet by conducting elements in the elongated member.

2. The apparatus of claim 1 wherein the segment of the elongated member is pleated.

3. The apparatus of claim 1 wherein the source of energy comprises a radio frequency generator.

4. The apparatus of claim 1 further comprising a feedback indicator.

5. The apparatus of claim 4 wherein the feedback indicator is an auditory signal.

6. The apparatus of claim 4 wherein the feedback indicator is a visual signal.

7. The apparatus of claim 4 wherein the feedback indicator is indicative of shrinkage.

8. The apparatus of claim 4 wherein the feedback indicator is indicative of temperature.

9. The apparatus of claim 4 wherein the feedback indicator is indicative of electrical characteristics.

* * * * *